United States Patent
Kim et al.

(10) Patent No.: US 10,753,797 B2
(45) Date of Patent: Aug. 25, 2020

(54) SPECTRUM PROCESSING APPARATUS AND SPECTRUM PROCESSING METHOD

(71) Applicant: SAMSUNG ELECTRONICS CO., LTD., Suwon-si (KR)

(72) Inventors: Sang Kyu Kim, Yongin-si (KR); Jun Ho Lee, Incheon (KR); Hyeong Seok Jang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 34 days.

(21) Appl. No.: 16/251,290

(22) Filed: Jan. 18, 2019

(65) Prior Publication Data

US 2020/0025612 A1    Jan. 23, 2020

(30) Foreign Application Priority Data

Jul. 20, 2018 (KR) .................... 10-2018-0084860

(51) Int. Cl.
  *G01J 3/26*    (2006.01)
  *G01N 21/359*  (2014.01)
  *G01J 3/28*    (2006.01)

(52) U.S. Cl.
  CPC .............. *G01J 3/26* (2013.01); *G01J 3/2803* (2013.01); *G01J 3/2823* (2013.01); *G01N 21/359* (2013.01)

(58) Field of Classification Search
  CPC ........ G01J 3/12; G01J 3/2803; G01N 21/359; G01N 33/66; A61B 5/14532; A61B 5/1455
  See application file for complete search history.

(56) References Cited

U.S. PATENT DOCUMENTS

| | | |
|---|---|---|
| 6,674,526 B1 * | 1/2004 | Marbach ............... G01J 3/2803 356/300 |
| 6,847,447 B2 | 1/2005 | Ozanich |
| 7,689,268 B2 | 3/2010 | Marshik-Geurts et al. |
| 9,171,355 B2 | 10/2015 | Zhuo et al. |
| 9,207,182 B2 | 12/2015 | Sato et al. |

(Continued)

FOREIGN PATENT DOCUMENTS

| | | |
|---|---|---|
| JP | 5927081 B2 | 5/2016 |
| JP | 6006036 B2 | 10/2016 |
| JP | 6080577 B2 | 2/2017 |

OTHER PUBLICATIONS

John Kalivas, "Calibration Maintenance and Transfer Using Tikhonov Regularization Approaches", 2009, (Year: 2009).*

(Continued)

*Primary Examiner* — Maurice C Smith
(74) *Attorney, Agent, or Firm* — Sughrue Mion, PLLC

(57) ABSTRACT

Provided is a spectrum processing apparatus for removing noise, caused by a change in external environment, from a spectrum obtained by a spectrometer. The spectrum processing apparatus includes: a spectrometer configured to measure a first spectrum according to a change in external environment from a first object, and to measure a second spectrum for component analysis from a second object; and a processor configured to extract, based on the first spectrum, an eigenvector for each wavelength according to the change in external environment, and to obtain a final spectrum by correcting the second spectrum based on the extracted eigenvector for each wavelength.

20 Claims, 14 Drawing Sheets

(56) References Cited

U.S. PATENT DOCUMENTS

| | | |
|---|---|---|
| 9,316,628 B2 | 4/2016 | O'Brien et al. |
| 9,360,366 B1 | 6/2016 | Tran |
| 9,395,244 B2 | 7/2016 | Kurokawa et al. |
| 9,933,305 B2 | 4/2018 | Goldring et al. |
| 2003/0023152 A1* | 1/2003 | Abbink ............... A61B 5/0075 600/316 |
| 2005/0261560 A1* | 11/2005 | Ridder ............... A61B 5/14546 600/310 |
| 2008/0220530 A1 | 9/2008 | Bahn et al. |
| 2014/0288885 A1 | 9/2014 | Morita |
| 2017/0059482 A1 | 3/2017 | Kim et al. |
| 2018/0020956 A1 | 1/2018 | Lee et al. |

OTHER PUBLICATIONS

Young Mee Jung, "Thermal Behavior of Langmuir-Blodgett Film of Poly(tert-butyl methacrylate) by Principal Component Analysis Based Two-Dimensional Correlation Spectroscopy", 2005 (Year: 2005).*

* cited by examiner

FIG. 3B

| TEMPERATURE(°C) | ABSORBANCE(a.u.) |
|---|---|
| 25 | 1.418 |
| 40 | 1.403 |
| 60 | 1.390 |
| 80 | 1.372 |

SPECTRUM PROCESSING APPARATUS AND SPECTRUM PROCESSING METHOD

CROSS-REFERENCE TO RELATED APPLICATION(S)

This application claims priority from Korean Patent Application No. 10-2018-0084860, filed on Jul. 20, 2018, in the Korean Intellectual Property Office, the entire disclosure of which is incorporated herein by reference for all purposes.

BACKGROUND

1. Field

Apparatuses and methods consistent with exemplary embodiments relate to a spectrum processing apparatus and a spectrum processing method, and more particularly to technology for removing noise, caused by a change in external environment, from a spectrum measured from an object.

2. Description of the Related Art

Research is being conducted on methods of measuring bio-information, such as blood glucose, in a non-invasive manner using Raman spectroscopy or near-infrared spectroscopy. A bio-information measuring apparatus using spectroscopy generally includes a light source which emits light onto an object, and a detector which detects an optical signal returning from the object. The bio-information measuring apparatus reconstructs a spectrum by using the optical signal detected by the detector, and measures in vivo components, such as blood glucose, calories, and the like, by analyzing the reconstructed spectrum. Generally, a scattered spectrum is affected by a change in temperature. In the case of a large-size spectrometer, the effect of temperature may be minimized since the large spectrometer has a temperature control system to control the temperature of a system itself, but it is difficult to provide such temperature control system for a small-size spectrometer.

SUMMARY

In one general aspect, there is provided a spectrum processing apparatus including: a spectrometer configured to measure a first spectrum according to a change in external environment from a first object, and to measure a second spectrum for component analysis from a second object; and a processor configured to extract, based on the first spectrum, an eigenvector for each wavelength according to the change in the external environment, and to obtain a final spectrum by correcting the second spectrum based on the extracted eigenvector for each wavelength.

In this case, the external environment may include temperature.

Further, the first object may not include a component to be analyzed, and the second object may include the component to be analyzed.

The processor may extract the eigenvector for each wavelength by using at least one of a Principal Component Analysis (PCA) method and a Singular Value Decomposition (SVD) method.

The processor may remove noise, caused by the external environment, from the second spectrum based on the extracted eigenvector for each wavelength by applying a noise removal method including a least square method.

The spectrometer may measure a third spectrum from a third object containing the component to be analyzed, wherein the processor may correct the third spectrum based on the eigenvector for each wavelength, and may obtain the final spectrum by subtracting the corrected third spectrum, which is obtained by correcting the third spectrum, from a corrected second spectrum which is obtained by correcting the second spectrum.

The spectrometer may include: one or more light sources configured to emit light onto the first object and the second object; and one or more detectors configured to detect light returning from the first object and the second object.

In this case, the one or more light sources may emit light of different wavelengths.

The processor may provide guide information to guide a user to measure the first spectrum according to the change in the external environment based on at least one predetermined criterion.

The spectrum processing apparatus may further include an output circuitry configured to output a processing result of the processor.

In addition, the spectrum processing apparatus may further include a communicator configured to transmit the processing result of the processor to an external device.

In this case, the component may include one or more of blood glucose, triglycerides, cholesterol, calories, proteins, and uric acid.

In another general aspect, there is provided a spectrum processing method including: measuring a first spectrum according to a change in external environment from a first object; extracting an eigenvector for each wavelength according to the change in the external environment based on the first spectrum; measuring a second spectrum for component analysis from a second object; and obtaining a final spectrum by correcting the second spectrum based on the extracted eigenvector for each wavelength.

In this case, the external environment may include temperature.

Further, the first object may include at least one of pure water and human skin in an empty stomach state, and the second object may include human skin in a non-empty stomach.

The extracting of the eigenvector for each wavelength may include extracting the eigenvector for each wavelength by using at least one of a Principal Component Analysis (PCA) method and a Singular Value Decomposition (SVD) method.

The obtaining of the final spectrum may include removing noise, caused by the external environment, from the second spectrum based on the extracted eigenvector by using a noise removal method including a least square method.

The spectrum processing method may further include: measuring a third spectrum from a third object containing the component to be analyzed; and correcting the third spectrum based on the eigenvector for each wavelength, wherein the obtaining of the final spectrum may include obtaining the final spectrum by subtracting the corrected third spectrum, which is obtained by correcting the third spectrum, from a corrected second spectrum which is obtained by correcting the second spectrum.

In addition, the spectrum processing method may further include providing guide information to guide a user to measure the first spectrum according to the change in the external environment based on at least one predetermined criterion.

Moreover, the spectrum processing method may further include outputting the final spectrum.

BRIEF DESCRIPTION OF THE DRAWINGS

The above and/or other aspects will become apparent and more readily appreciated by describing certain exemplary embodiments with reference to the accompanying drawings.

FIGS. 3A to 3G are diagrams explaining a spectrum processing process according to an embodiment.

Figure 1:
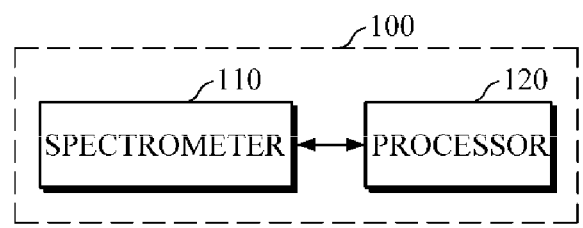
FIG. 1 is a block diagram illustrating a spectrum processing apparatus according to an embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Details of other embodiments are included in the following detailed description and drawings. Advantages and features of the invention, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part', 'unit' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Hereinafter, embodiments of a spectrum processing apparatus and spectrum processing method will be described in detail with reference to the accompanying drawings.

Various embodiments of the spectrum processing apparatus which will be described below may be embedded in various information processing devices such as a mobile wearable device, a smart device, and the like. Examples of the various information processing devices may include, but are not limited to, a wearable device of various types such as a smart watch worn on the wrist, a smart band-type wearable device, a headphone-type wearable device, a hair-band-type wearable device, and the like, a mobile device such as a smartphone, a tablet personal computer (PC), and the like, or a specialized medical institution system, and the like.

FIG. 1 is a block diagram illustrating a spectrum processing apparatus according to an embodiment.

Referring to FIG. 1, the spectrum processing apparatus 100 includes a spectrometer 110 and a processor 120.

The spectrometer 110 may measure a spectrum from an object. The spectrometer 110 may measure a spectrum using Raman spectroscopy or near-infrared spectroscopy. The spectrometer 110 may include one or more light sources which emit light onto an object, and one or more detectors which detect light scattered or reflected from the object.

The one or more light sources may include a light emitting diode (LED), a laser diode, a fluorescent body, and the like. The plurality of light sources may emit light of different wavelengths, in which case a color filter may be disposed on the top of at least some of the light sources to transmit or block light in a specific wavelength region. The detector may include one pixel or a pixel array including two or more pixels, in which each pixel may include a photo diode or a photo transistor. Upon detecting light, the detector may convert the detected light signal into an electric signal. A light focusing device, such as a microlens, for improving light focusing ability, may be disposed on the top of each pixel.

The processor 120 may be electrically connected to the spectrometer 110, and may control the spectrometer 110 in response to a request for measuring a spectrum. Further, upon receiving a signal from the spectrometer 110, the processor 120 may recover a spectrum of an object by using the received signal. The reconstructed spectrum may be used to analyze components of an object. In this case, the components of an object may include blood glucose, calories, alcohol, triglycerides, proteins, cholesterol, uric acid, and the like, but are not limited thereto.

Once a spectrum is measured for analyzing components of an object, the processor 120 may perform various spectrum processing operations, such as removing noise, caused by a change in external environment, from the measured spectrum, and the like. In this case, the change in external environment may include various factors, such as temperature, humidity, and the like, which affect accuracy of a spectrum. For convenience of explanation, the following description will be made with respect to a change in temperature as an example.

For example, once the spectrometer 110 measures a first spectrum, in which characteristics of a change in external environment are reflected, from a first object, the processor 120 may extract characteristics for each wavelength of the spectrometer 110 according to the change in external environment by using the first spectrum. In this case, the first object may be an object used as a reference for obtaining a background spectrum, and may not include a component to be analyzed, e.g., glucose. For example, the first object may include, but not limited to, pure water containing no glucose or human skin in an empty stomach state of a human.

Further, once the spectrometer 110 measures a second spectrum for component analysis from a second object, the processor 120 may obtain a final spectrum by correcting the second spectrum based on the first spectrum. For example, the processor 120 may remove noise, caused by an external environment, from the second spectrum based on the characteristics for each wavelength of the spectrometer 110 which are extracted using the first spectrum. In this case, the second object may be a human skin tissue and the like for use in analyzing components (e.g., human skin in a non-empty stomach state), and may include a component to be analyzed. For example, the second object may be a portion of the radial artery, a top portion of the wrist where veins or capillaries pass, fingers, and the like.

The processor 120 may control the spectrometer 110 to obtain the first spectrum from the first object. In this case, the first spectrum may be measured at the time of manufacturing the spectrum processing apparatus 100 or at the request of a user under circumstances where various changes occur in an external environment. Further, the processor 120 may determine whether to measure the first spectrum according to at least one predetermined criterion; and upon determining to measure the first spectrum, the processor 120 may provide a guide (or guide information) to a user to measure the first spectrum. For example, according to at least one predetermined criterion, which includes determination that a sensitivity of the final spectrum is not sufficiently high, determination that a result of analysis of an object's component using the final spectrum is not accurate, and the like, the processor 120 may determine to re-measure the first spectrum and output guide information to the user to measure the first spectrum again.

The spectrometer 110 may be controlled by the processor 120 to obtain the first spectrum, in which characteristics of a temperature change are reflected, by repeatedly measuring spectra from the first object for a sufficient period of time in an external environment, e.g., a temperature changing environment. The first spectrum obtained in this manner may be stored in a storage module (or a storage) to be used for correcting the second spectrum. In this case, the measurement may be made by artificially changing the external environment or under circumstances where an environment naturally changes.

Further, upon receiving a request for measuring the second spectrum for component analysis, the processor 120 may control the spectrometer 110 to measure the second spectrum from the second object. In this case, the request for measuring the second spectrum may be input intermittently by a user. Alternatively, a measurement time interval may be preset for the spectrum processing apparatus 100 to measure the second spectrum such that the second spectrum is measured continuously at regular time intervals.

For example, the processor 120 may remove noise from the second spectrum based on the first spectrum by using a Principal Component Analysis (PCA) method, a Singular Value Decomposition (SVD) method, a Least Square method, and the like. For example, the processor 120 may extract an eigenvector for each wavelength, in which characteristics of a change in external environment are reflected, from the first spectrum by using the PCA method, the SVD method, and the like. In addition, the processor 120 may remove noise, caused by the change in external environment, from the second spectrum based on the eigenvector for each wavelength.

In another example, the spectrometer 110 may measure a third spectrum from a third object. In this case, the third object may include a water solution or human skin containing a component (e.g., glucose) to be analyzed, and the like, but is not limited thereto. Driving conditions of the light sources of the spectrometer 110 and/or a spectrum measuring environment may be the same as a measuring environment of the second spectrum for component analysis. The processor 120 may correct the second spectrum and the third spectrum based on the eigenvector for each wavelength, and may obtain a final spectrum by subtracting the third spectrum from the second spectrum.

As described above, the final spectrum obtained by the spectrum processing process may be stored in a storage module to be used for analyzing components of an object, or may be transmitted to an external device such as a wearable device, a smartphone, a tablet PC, a laptop computer, a desktop computer, an information processing system of a medical institution, and the like.

Figure 2:
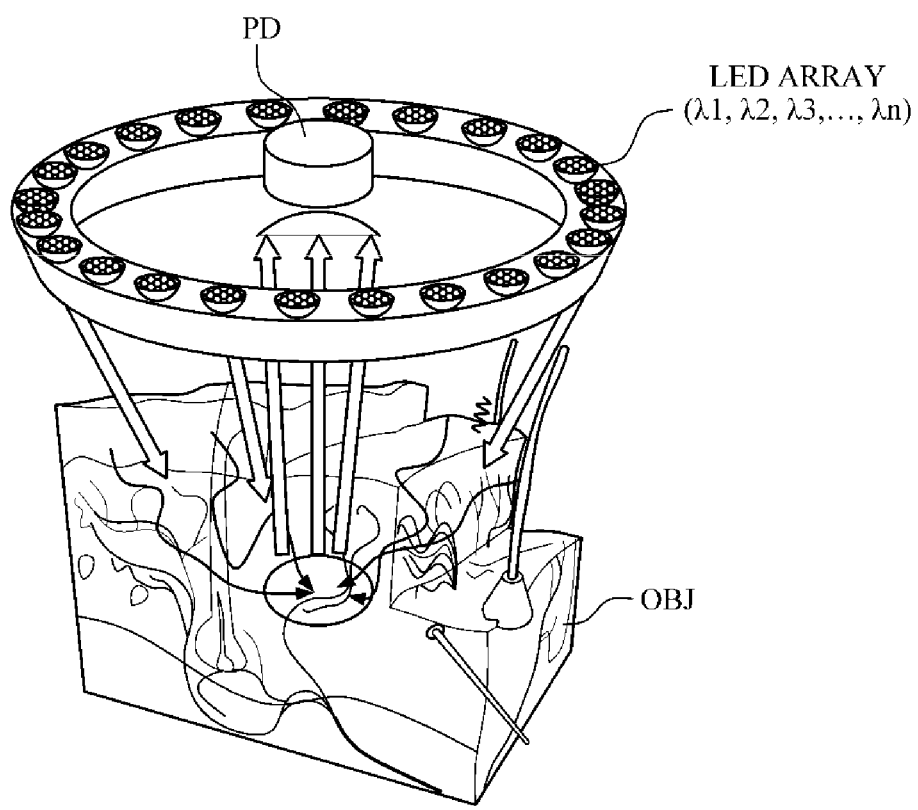
FIG. 2 is a diagram schematically illustrating a structure of a spectrometer according to an embodiment.

FIG. 2 is a diagram schematically illustrating a structure of a spectrometer according to an embodiment.

Referring to FIGS. 1 and 2, the spectrometer 110 includes an LED array having N number of LED light sources arranged on a circular frame. Further, a photodiode detector PD may be disposed at the center of the circular frame. Here, a shape of the frame is not limited to a circular shape, and may be modified depending on devices in which the spectrum processing apparatus 100 is mounted.

Each LED light source may have at least some of peak wavelengths $\lambda_1, \lambda_2, \lambda_3, \ldots$, and $\lambda_n$ in different wavelength bands. The peak wavelengths of each LED light source may be preset, and may be set based on a spectrum measurement portion, a component to be analyzed, and the like.

Each LED light source may sequentially emit the wavelengths $\lambda_1, \lambda_2, \lambda_3, \ldots$, and $\lambda_n$ onto the object OBJ in a time-division manner. In this case, driving conditions of light sources, which include a driving sequence, a driving time, and the like of light sources, may be preset. After light is emitted by each of the LED light sources onto the object OBJ for component analysis, the emitted light is absorbed into, or reflected or scattered from, the object OBJ depending on tissue properties of the object OBJ. In this case, photoreaction properties of the object OBJ may vary depending on the types of the object OBJ and the wavelengths of light, and the degree of absorption, reflection, transmission, or scattering of light by the object OBJ may vary depending on the photoreaction properties of the object OBJ.

The processor 120 may obtain a linearly independent equation based on a data set of signals according to a response of the object OBJ detected by the detector PD, and may recover a spectrum based on the linearly independent equation. For example, the processor 120 may obtain a linear equation written in matrix form as represented by the following Equation 1, and may obtain the recovered spectrum by using a method of solving the linear equation.

$$Az = U \qquad \text{[Equation 1]}$$

Herein, A is a matrix of properties of a reference spectrum measured according to driving conditions of each light source; U is a matrix of values actually measured from the object OBJ for component analysis under the same driving conditions of each light source; and z is a spectrum to be recovered. In this case, there may be an ill-conditioned matrix A, in which a solution of Equation 1, which is a linear equation, may be incorrect. Therefore, a spectrum of an object may be recovered by using a solution to an inverse problem, which imposes no limitations on the resolution size of the spectrum, and recovered with high accuracy by using a minimum number of used spectrum curves. In this case, the Tikhonov regularization method used to solve the inverse problem may be represented by the following Equation 2.

$$(\alpha E + A^T A) Z_\alpha = A^T u$$

$$Z_\alpha = (\alpha E + A^T A)^{-1} A^T u \qquad \text{[Equation 2]}$$

Herein, u is each component of a matrix U actually measured by the detector; E is a unit matrix; A is a kernel matrix, and a matrix of a reference spectrum measured under the driving conditions of each light source; and α is a unit of noise removal. The Equation 2 may be solved using any known method, e.g., a least square method which may be solved using, e.g., QR decomposition.

FIGS. 3A to 3G are diagrams explaining a spectrum processing process according to an embodiment.

Referring to FIGS. 1 to 3G, an example where the spectrum processing apparatus 100 processes a spectrum according to a change in temperature will be described below.

Figure 3A:
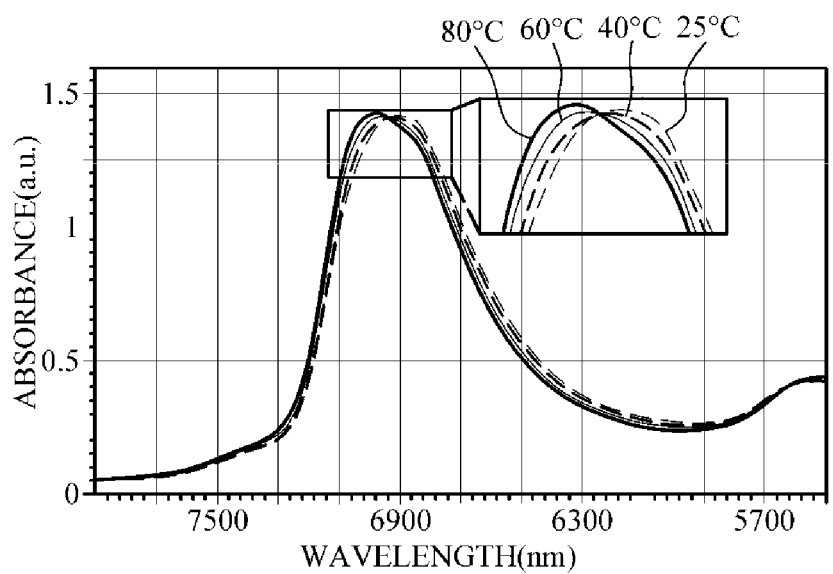

FIGS. 3A and 3B are diagrams illustrating a change in absorbance of a spectrum according to a change in temperature. As illustrated in FIGS. 3A and 3B, a spectrum obtained by the spectrometer 110 is affected by a change in temperature, in which in the case of near-infrared spectroscopy, when temperature is changed by 1° C., absorbance of a spectrum is generally changed by about $10^{-3}$. Accordingly, in an environment where temperature is not maintained at a constant level, it may be difficult to obtain a spectrum with high sensitivity by using the spectrometer 110. Thus, it is required to correct characteristics for each wavelength according to a change in external environment such as temperature.

Figure 3C:
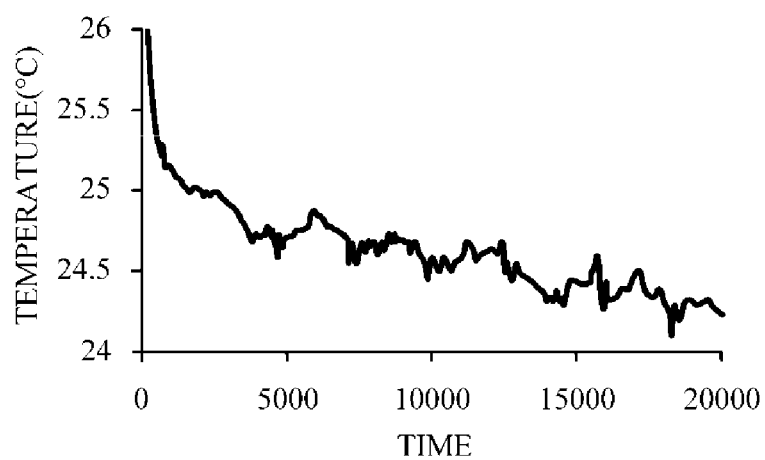
Figure 3D:
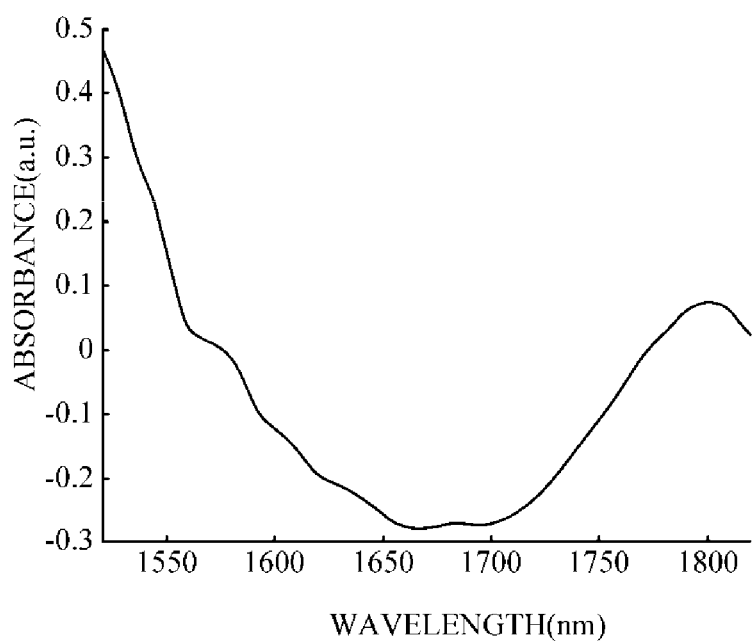

FIG. 3C is a diagram illustrating an example of a change in external environment while a background spectrum used as a reference is obtained. As illustrated in FIG. 3C, temperature is gradually decreased over time from 26° C. to 24° C. FIG. 3D is a diagram illustrating a background spectrum measured in an environment where temperature is changed as illustrated in FIG. 3C, in which case the background spectrum may be a spectrum measured from a pure water solution containing no component to be analyzed. The background spectrum may be measured while temperature is artificially changed in a laboratory by simulating an environment where the spectrum processing apparatus 100 is to be used, or may be measured in an actual environment, where the spectrum processing apparatus 100 is used in practice, for a predetermined period of time during which temperature is changed.

Figure 3E:
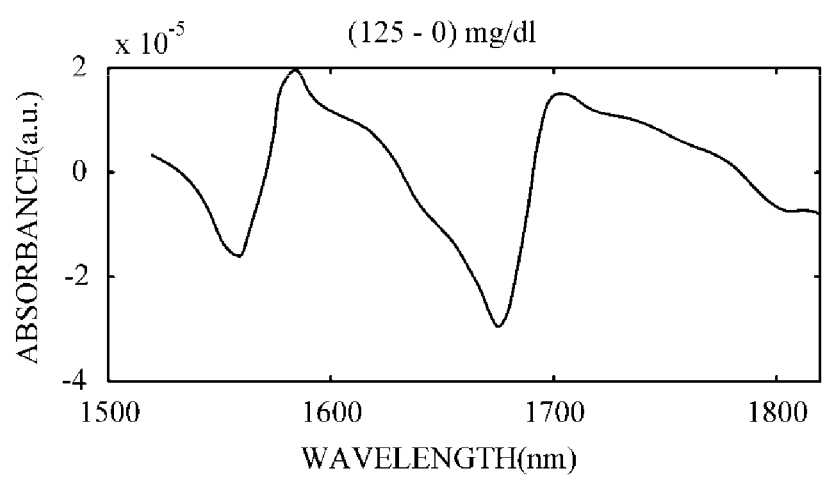
Figure 3F:
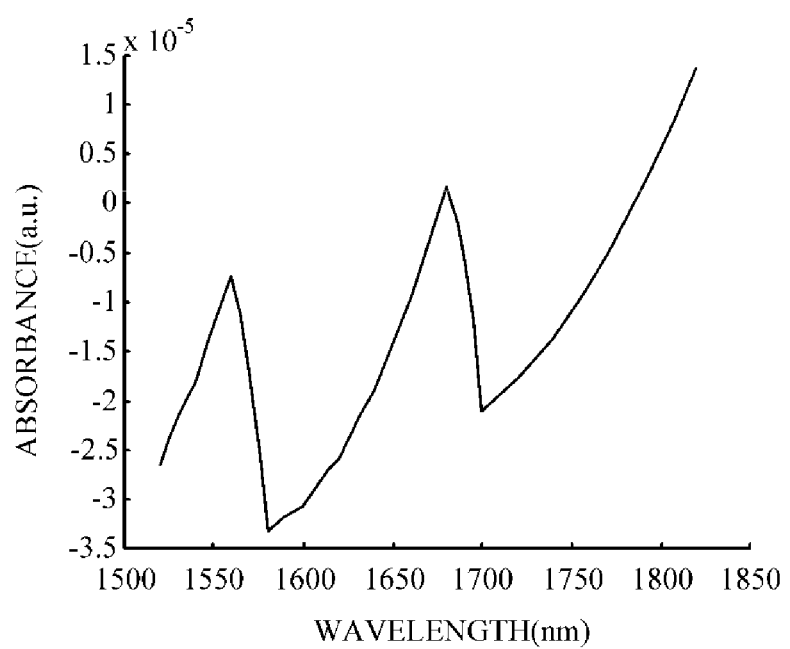

FIG. 3E is a diagram illustrating a spectrum measured from human skin for component analysis. Noise, caused by an external environment including temperature, is reflected in the measured spectrum. FIG. 3F is a diagram illustrating an eigenvector for each wavelength, which is extracted from the background spectrum of FIG. 3D by using the Principal Component Analysis (PCA) method and/or the Singular Value Decomposition (SVD) method, and which includes characteristics according to a change in external environment.

Figure 3G:
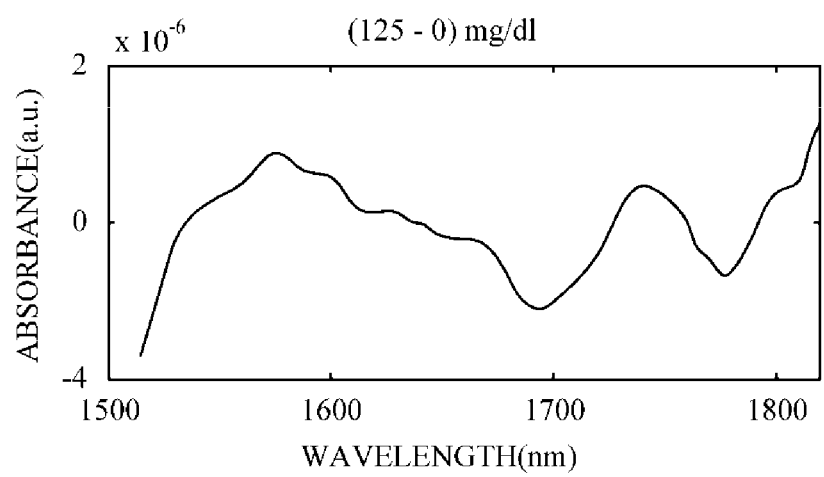

FIG. 3G is a diagram illustrating a spectrum, which is obtained by removing noise from the spectrum of FIG. 3E by using the eigenvector for each wavelength of FIG. 3F. In this case, the processor 120 may obtain the spectrum of FIG. 3G by applying a least square method and the like.

Figure 4:
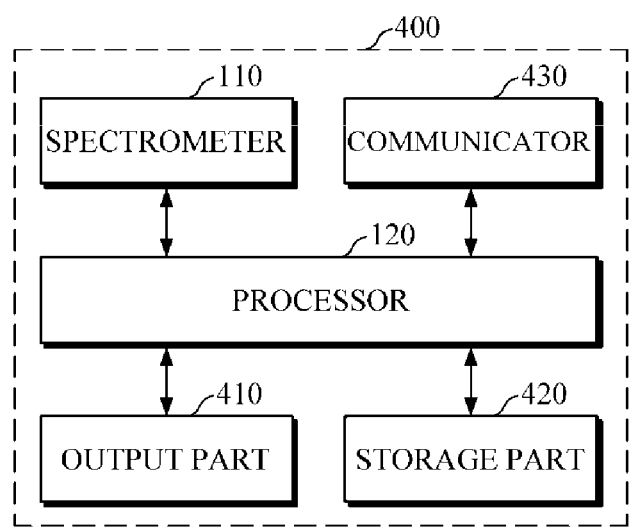
FIG. 4 is a block diagram illustrating a spectrum processing apparatus according to another embodiment.

FIG. 4 is a block diagram illustrating a spectrum processing apparatus according to another embodiment.

Referring to FIG. 4, the spectrum processing apparatus 400 includes a spectrometer 110, a processor 120, an output part (or output circuitry) 410, a storage part 420, and a communicator 430. In this case, the spectrometer 110 and the processor 102 are described above in detail, such that the following description will be made based on non-overlapping details.

The output part 410 may output various types of information processed by the processor 120. The output part 410 may include a visual output module such as a display comprising circuitry and the like, an audio output module such as a speaker comprising circuitry and the like, a haptic module generating vibration or tactile sensation, and the like. For example, the output part 410 may output a final spectrum. In this case, the output part 410 may output a first spectrum, a second spectrum, and a third spectrum along with each corrected spectrum thereof.

The storage part 420 may store user feature information, information on driving conditions of light sources of the spectrometer 110, and the like. Further, the storage part 420 may store a processing result of the processor 120. For example, the storage part 420 may store a background spectrum, an eigenvector for each wavelength, a spectrum for component analysis before noise is removed therefrom, a spectrum for component analysis after noise is removed therefrom, and the like.

The storage part 420 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communicator 430 may be connected to an external device through wired and wireless communications, and may receive various types of information from the external device. Examples of the external device may include an information processing device such as a smartphone, a tablet PC, a laptop computer, a desktop computer, and the like, but the external device is not limited thereto, and may have, if necessary, a function of analyzing components of an object.

For example, the communicator 430 may receive a request for measuring a spectrum for component analysis of an object from the external device, and may transmit the received request to the processor 120. In this case, the processor 120 may control the spectrometer 110 in response to the request for measuring the spectrum. Further, the communicator 430 may receive reference information, such as the driving conditions of the light sources and the like, from the external device, and may transmit the received reference information to the processor 120. In this case, the processor 120 may store the received reference information in the storage part 420. In addition, the communicator 430 may transmit a processing result of the processor 120 to the external device.

The communicator 430 may communicate with the external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 5:
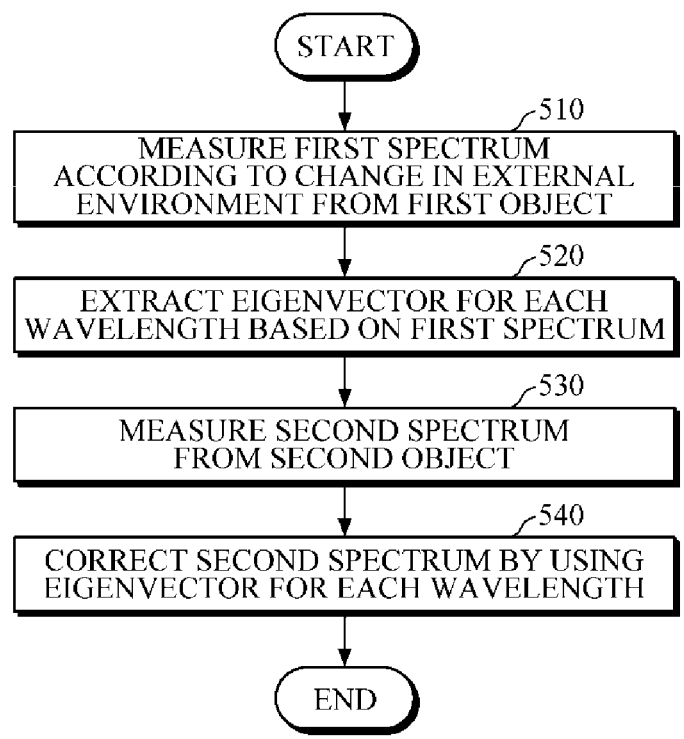
FIG. 5 is a flowchart illustrating a spectrum processing method according to an embodiment.

FIG. 5 is a flowchart illustrating a spectrum processing method according to an embodiment.

The spectrum processing method of FIG. 5 is an example of a spectrum processing method performed by any one of the spectrum processing apparatuses 100 and 400 described above.

Referring to FIG. 5, the spectrum processing apparatus may measure a first spectrum according to a change in external environment from a first object used as a reference in 510. In this case, the first object may include a pure water solution, human skin in an empty stomach state, and the like, but is not limited thereto. The change in external environment may include a change in temperature, and the spectrum processing apparatus may repeatedly measure the first spectrum while changing temperature under the same driving conditions of the light sources. The first spectrum may be measured at the request of a user or when a predefined criterion is satisfied.

Then, the spectrum processing apparatus may extract an eigenvector for each wavelength based on the first spectrum in 520. In this case, the eigenvector for each wavelength may include noise characteristics according to the change in external environment. For example, the spectrum processing apparatus may extract the eigenvector for each wavelength from the first spectrum by using the Principal Component Analysis (PCA) method and/or the Singular Value Decomposition (SVD) method.

Subsequently, the spectrum processing apparatus may measure a second spectrum from a second object in 530. A request for measuring the second spectrum may be input by a user or an external device, or may be generated at predetermined time intervals. The second object may be human skin for analyzing components such as blood glucose, calories, alcohol, triglycerides, proteins, cholesterol, uric acid, and the like, but is not limited thereto. In this case, since the second spectrum is measured in a normal environment, the second spectrum measured from the second object may include noise caused by an external environment.

Next, the spectrum processing apparatus may correct the second spectrum by using the eigenvector for each wavelength in 540. For example, the spectrum processing apparatus may remove noise for each wavelength from the second spectrum by using the eigenvector for each wavelength, and by using the least square method and the like. A third spectrum, obtained as a result of correcting the second spectrum in this manner, may be stored in a storage module to be used for analyzing components of an object.

Figure 6:
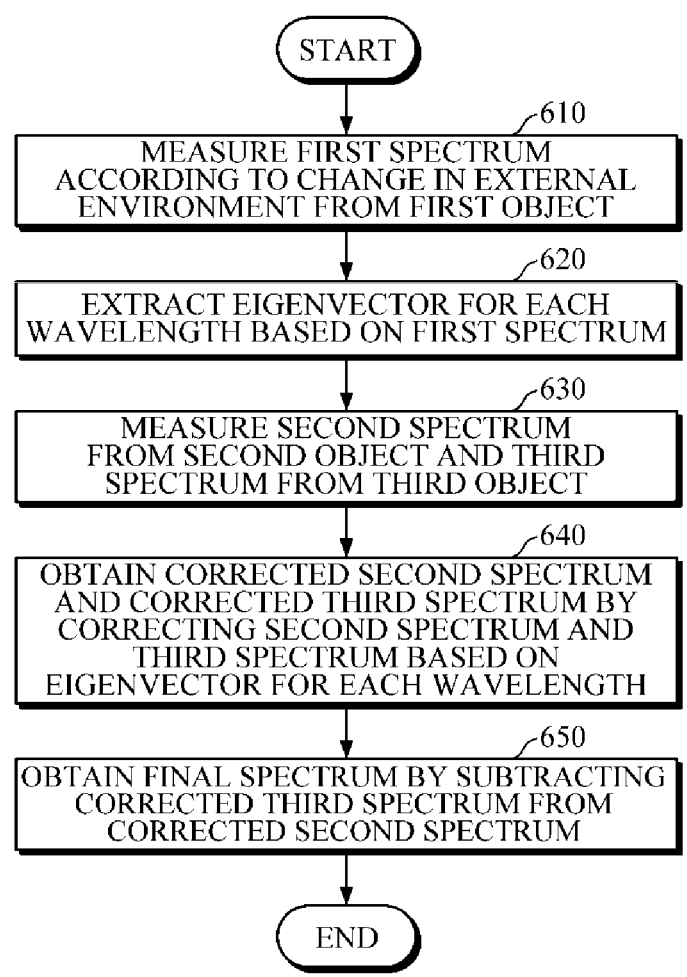
FIG. 6 is a flowchart illustrating a spectrum processing method according to another embodiment.

FIG. 6 is a flowchart illustrating a spectrum processing method according to another embodiment.

The spectrum processing method of FIG. 6 is an example of a spectrum processing method performed by any one of the aforementioned spectrum processing apparatuses 100 and 400, which will be briefly described below in order to avoid duplication of explanation.

Referring to FIG. 6, the spectrum processing apparatus may repeatedly measure a first spectrum according to a change in external environment, such as temperature, from a first object used as a reference in 610.

Then, the spectrum processing apparatus may extract an eigenvector for each wavelength based on the measured first spectrum in 620. In this case, the spectrum processing apparatus may extract the eigenvector for each wavelength by using the Principal Component Analysis (PCA) method and/or the Singular Value Decomposition (SVD) method, but is not limited thereto.

Subsequently, the spectrum processing apparatus may measure a second spectrum from a second object and a third spectrum from a third object in 630. In this case, the second object may be a human skin tissue and the like for component analysis; and the third object may be a water solution containing a component to be analyzed, and the like. The second spectrum and the third spectrum may be measured at different times. For example, the third spectrum may be measured in advance and stored, and may be used every time the second spectrum is measured.

Next, by correcting the second spectrum and the third spectrum based on the eigenvector for each wavelength which is extracted in 620, the spectrum processing apparatus may obtain the corrected second spectrum and the corrected third spectrum in 640. In this case, the spectrum processing apparatus may obtain each corrected spectrum by using the least square method and the like. Further, the corrected second spectrum and the corrected third spectrum are not necessarily required to be obtained at the same time, but may be obtained each time the second spectrum and the third spectrum are measured.

Then, the spectrum processing apparatus may obtain a final spectrum by subtracting the corrected third spectrum from the corrected second spectrum in 650.

Figure 7:
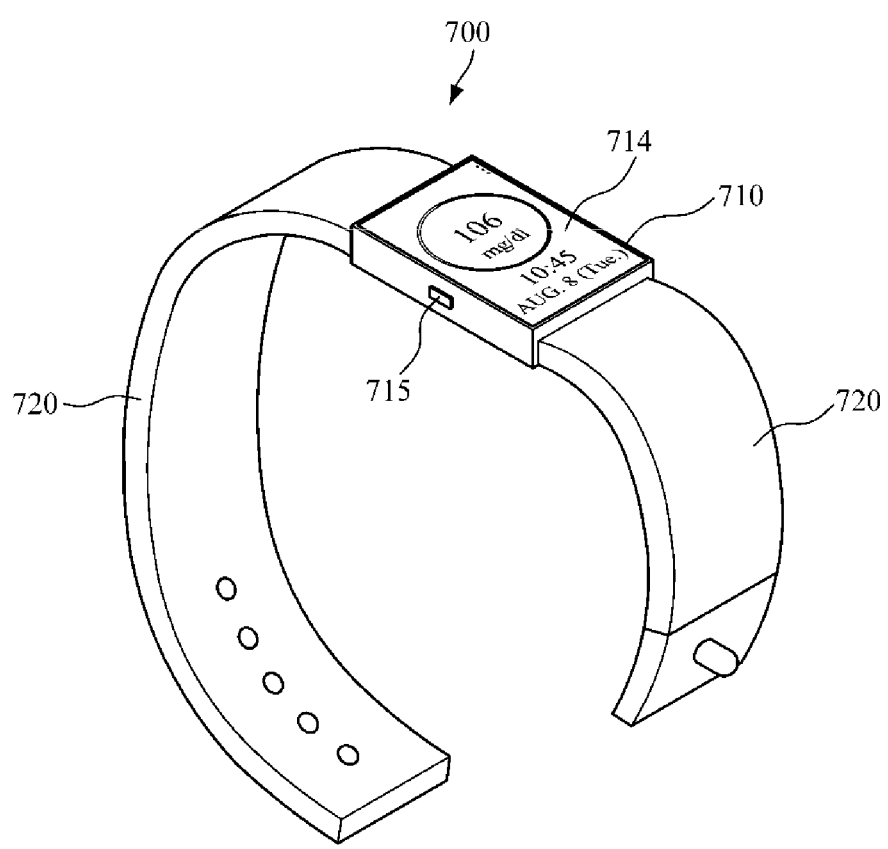
FIG. 7 is a diagram schematically illustrating a structure of a biological component analyzing apparatus according to an embodiment.
Figure 8:
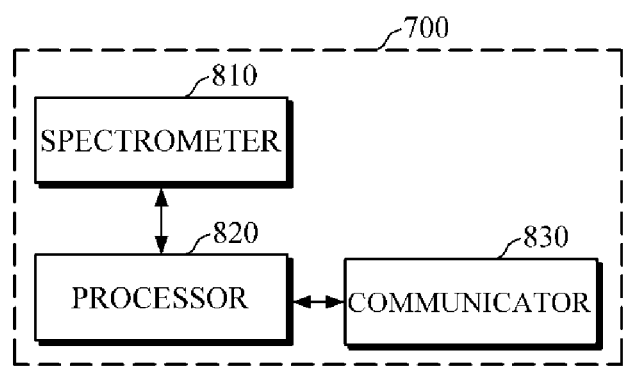
FIG. 8 is a block diagram illustrating the biological component analyzing apparatus of FIG. 7.

FIG. 7 is a diagram schematically illustrating a structure of a biological component analyzing apparatus according to an embodiment. FIG. 8 is a block diagram illustrating the biological component analyzing apparatus of FIG. 7.

As illustrated in FIG. 7, an example of the biological component analyzing apparatus 700 may be a wearable device in the form of a smart watch. However, the wearable device is not limited thereto, and may be modified in various forms such as a smartphone, a tablet PC, a smart band, and the like. The biological component analyzing apparatus 700 of FIGS. 7 and 8 may include the aforementioned spectrum processing technique.

Referring to FIGS. 7 and 8, the biological component analyzing apparatus 700 includes a main body 710 and a strap 720.

The strap 720 may be connected to the main body 710, and may be flexible such that the strap 720 may be bent around a user's wrist or may be bent in a manner which allows the strap 720 to be detached from the user's wrist. In this case, a battery, which supplies power to the biological component analyzing apparatus 700, may be embedded in the main body 710 or the strap 720.

Further, the biological component analyzing apparatus 700 may include a spectrometer 810 and a processor 820 which are mounted in the main body 710. As illustrated above with reference to FIG. 2, the spectrometer 810 may include a light source having an array of a plurality of LEDs and a detector, and may be disposed at a rear surface of the main body 710 that comes into contact with a top portion of a user's wrist.

The spectrometer 810 may emit light onto skin of a user by driving the light source according to a control signal of the processor 820, and may obtain a spectrum by detecting light returning from the skin. In this case, the light source may be configured to emit light in a near-infrared range or a mid-infrared range. The spectrometer 810 may include a Linear Variable Filter (LVF). The LVF has spectral properties which vary linearly over the entire length. Accordingly, the LVF may scatter the incident light in order of wavelengths. Therefore, the LVF, which has a compact size can achieve excellent light scattering ability.

At the request of a user or when a predefined criterion is satisfied, the processor 820 may control the spectrometer 810 to obtain a background spectrum from an object used as a reference. In this case, if a predefined criterion is satisfied, the processor 820 may provide guide information for a user to measure the background spectrum, and when the user completes preparation for measuring the background spectrum, the processor 820 may control the spectrometer 810. The object used as a reference may be a pure water solution containing no component to be analyzed such as glucose. Alternatively, the user may measure the background spectrum in an empty stomach state while wearing the spectrum processing apparatus 100, e.g., on the wrist.

Once the background spectrum is measured, in which the change in external environment is reflected, the processor 820 may extract an eigenvector for each wavelength by using the PCA method and/or the SVD method. The extracted eigenvector for each wavelength may be stored in a storage module.

In addition, at the request of a user or at predetermined measurement intervals, the processor 820 may measure a spectrum for component analysis from an object (e.g., skin of the wrist if a user wears the spectrum processing apparatus 100 on the wrist), and may obtain a final spectrum by removing noise from the measured spectrum based on the eigenvector for each wavelength. In this case, the processor 820 may remove noise by using the least square method and the like.

The processor 820 may analyze components, such as blood glucose, calories, and the like, by using the final spectrum, from which noise caused by the change in external environment is removed. In this case, an estimation model may be built appropriately depending on components to be analyzed, and the processor 820 may analyze desired components by using the final spectrum and the estimated model. For example, for the analysis of blood glucose, a blood glucose estimation model may be provided by using the Beer-Lambert law.

The biological component analyzing apparatus 700 may further include a manipulator 715 and a display 714 which are mounted in the main body 710. The manipulator 715 receives a user command and transmits the received command to the processor 820. The manipulator 715 may include a power button to turn on/off the biological component analyzing apparatus 700.

Under the control of the processor 820, the display 714 may provide additional information, such as an analysis result of components, warning and alarm information, and the like, to a user by various visual methods.

Further, the biological component analyzing apparatus 700 may include a communicator 830 to communicate with an external device such as a user's mobile terminal, a smartphone, a tablet PC, a desktop computer, a laptop computer, and the like. The communicator 830 may be mounted in the main body 710.

According to the embodiments described above, accuracy may be further improved compared to a case where blood glucose values are calculated using a spectrum obtained by applying multiplicative scatter correction (MSC).

The disclosure can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the disclosure can be easily deduced by one of ordinary skill in the art.

At least one of the components, elements, modules or units described herein may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like.

The disclosure has been described herein with regard to exemplary embodiments. However, it will be obvious to those skilled in the art that various changes and modifications can be made without changing technical ideas and essential features of the disclosure. Thus, it is clear that the above-described embodiments are illustrative in all aspects and are not intended to limit the disclosure.

What is claimed is:

1. A spectrum processing apparatus, comprising:
a spectrometer configured to measure a first spectrum according to a change in external environment from a first object, and to measure a second spectrum for component analysis from a second object; and
a processor configured to extract, based on the first spectrum, an eigenvector for each wavelength according to the change in the external environment, and to obtain a final spectrum by correcting the second spectrum based on the extracted eigenvector for each wavelength.

2. The apparatus of claim 1, wherein the external environment comprises temperature.

3. The apparatus of claim 1, wherein the first object does not comprise a component to be analyzed, and the second object comprises the component to be analyzed.

4. The apparatus of claim 1, wherein the processor is further configured to extract the eigenvector for each wavelength by using at least one of a Principal Component Analysis (PCA) method and a Singular Value Decomposition (SVD) method.

5. The apparatus of claim 1, wherein the processor is further configured to remove noise, caused by the external environment, from the second spectrum based on the extracted eigenvector for each wavelength by applying a noise removal method, the noise removal method comprising a least square method.

6. The apparatus of claim 1, wherein the spectrometer is further configured to measure a third spectrum from a third object containing the component to be analyzed,
wherein the processor is further configured to correct the third spectrum based on the eigenvector for each wavelength, and obtain the final spectrum by subtracting a corrected third spectrum, which is obtained by correcting the third spectrum, from a corrected second spectrum which is obtained by correcting the second spectrum.

7. The apparatus of claim 1, wherein the spectrometer comprises:
one or more light sources configured to emit light onto the first object and the second object; and
one or more detectors configured to detect light returning from the first object and the second object.

8. The apparatus of claim 7, wherein the one or more light sources emit light of different wavelengths.

9. The apparatus of claim 1, wherein the processor is further configured to provide guide information to guide a user to measure the first spectrum according to the change in the external environment based on at least one predetermined criterion.

10. The apparatus of claim 1, further comprising an output circuitry configured to output a processing result of the processor.

11. The apparatus of claim 1, further comprising a communicator configured to transmit a processing result of the processor to an external device.

12. The method of claim 1, wherein the component comprises one or more of blood glucose, triglycerides, cholesterol, calories, proteins, and uric acid.

13. A spectrum processing method, comprising:
measuring a first spectrum according to a change in external environment from a first object;
extracting, based on the first spectrum, an eigenvector for each wavelength according to the change in the external environment;
measuring a second spectrum for component analysis from a second object; and
obtaining a final spectrum by correcting the second spectrum based on the extracted eigenvector for each wavelength.

14. The method of claim 13, wherein the external environment comprises temperature.

15. The method of claim 13, wherein the first object comprises at least one of pure water and human skin in an empty stomach state, and the second object comprises human skin in a non-empty stomach state.

16. The method of claim 13, wherein the extracting of the eigenvector for each wavelength comprises extracting the eigenvector for each wavelength by using at least one of a Principal Component Analysis (PCA) method and a Singular Value Decomposition (SVD) method.

17. The method of claim 13, wherein the obtaining of the final spectrum comprises removing noise, caused by the external environment, from the second spectrum based on the extracted eigenvector by using a noise removal method, the noise removal method comprising a least square method.

18. The method of claim 13, further comprising:
measuring a third spectrum from a third object containing the component to be analyzed; and
correcting the third spectrum based on the eigenvector for each wavelength,
wherein the obtaining of the final spectrum comprises obtaining the final spectrum by subtracting the corrected third spectrum, which is obtained by correcting the third spectrum, from a corrected second spectrum which is obtained by correcting the second spectrum.

19. The method of claim 13, further comprising providing guide information to guide a user to measure the first spectrum according to the change in the external environment based on at least one predetermined criterion.

20. The method of claim 13, further comprising outputting the final spectrum.

* * * * *